(12) United States Patent
Sorribes

(10) Patent No.: US 7,093,600 B2
(45) Date of Patent: Aug. 22, 2006

(54) DEVICE FOR NON-INVASIVELY CORRECTING THE SHAPE OF A HUMAN EXTERNAL EAR

(76) Inventor: Michael Miravet Sorribes, Jyllingeparken 156, Jyllinge 4040 (DK)

( * ) Notice: Subject to any disclaimer, the term of this patent is extended or adjusted under 35 U.S.C. 154(b) by 415 days.

(21) Appl. No.: 10/050,618

(22) Filed: Jan. 16, 2002

(65) Prior Publication Data

US 2002/0062110 A1    May 23, 2002

Related U.S. Application Data

(63) Continuation of application No. PCT/DK00/00421, filed on Jul. 25, 2000.

(30) Foreign Application Priority Data

Jul. 27, 1909   (DK) ............................... 1999 01068

(51) Int. Cl.
*A61F 11/00*   (2006.01)
(52) U.S. Cl. ..................................... 128/864; 128/865
(58) Field of Classification Search ........ 128/864–868, 128/898; 602/41, 42, 58
See application file for complete search history.

(56) References Cited

U.S. PATENT DOCUMENTS 1,338,090 A  *  4/1920  Parvin
4,187,838 A     2/1980  Dubrowski ................ 128/76 R
5,000,172 A  *  3/1991  Ward ............................ 602/52
5,076,262 A    12/1991  Coffey ........................ 128/76 R
5,295,950 A  *  3/1994  Godley ........................ 602/53
6,277,458 B1 *  8/2001  Dirksing .................... 428/42.3

FOREIGN PATENT DOCUMENTS

| CH | 208142 | 4/1940 |
| FR | 2743718 | 7/1997 |
| GB | 10220 | 4/1911 |
| GB | 2 304 579 A | 3/1997 |
| WO | WO 94/09731 | 5/1994 |
| WO | WO 00/09050 | 2/2000 |

\* cited by examiner

*Primary Examiner*—Michael A. Brown
(74) *Attorney, Agent, or Firm*—Winston & Strawn LLP

(57) ABSTRACT

A device for non-invasively correcting a human external ear is disclosed. The device comprises a flat fixture with an adhesive for sticking the fixture together with two fold parts on an ear which is folded about a folding line along a zone which is to be corrected with a permanent deformation. The fixture can be fixed on the ear easily and conveniently. In attached state, it is hardly visible, and the patient does not feel the fixture as something unpleasant and irritating to wear. The fixture can advantageously be used for correcting a small child's jug-ear which particularly easily can be given a permanent shape within the first few weeks after birth where the concentration of oestradiol is highest.

18 Claims, 9 Drawing Sheets

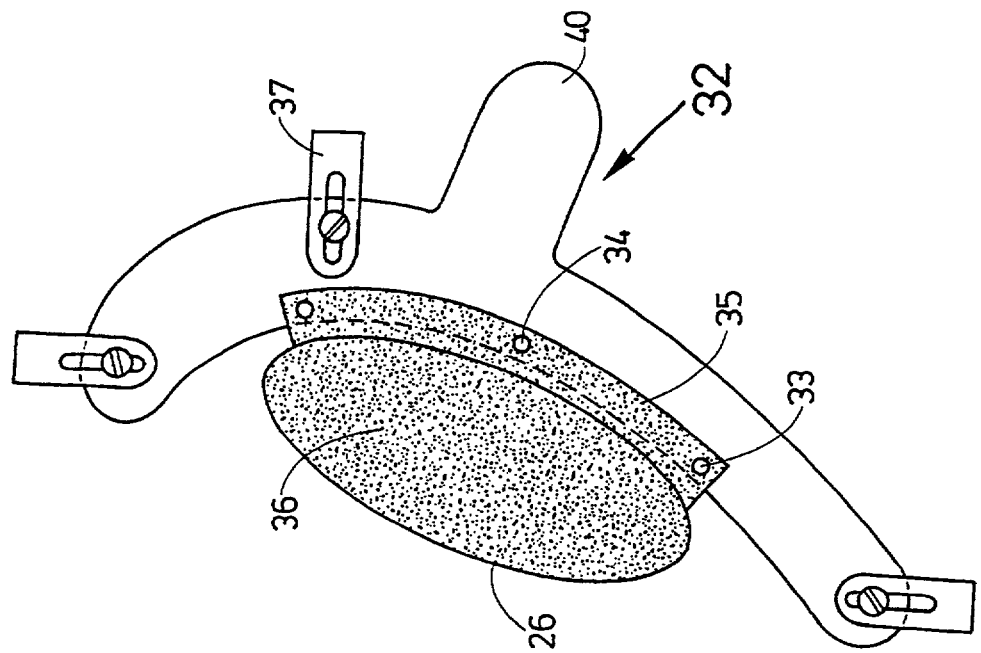
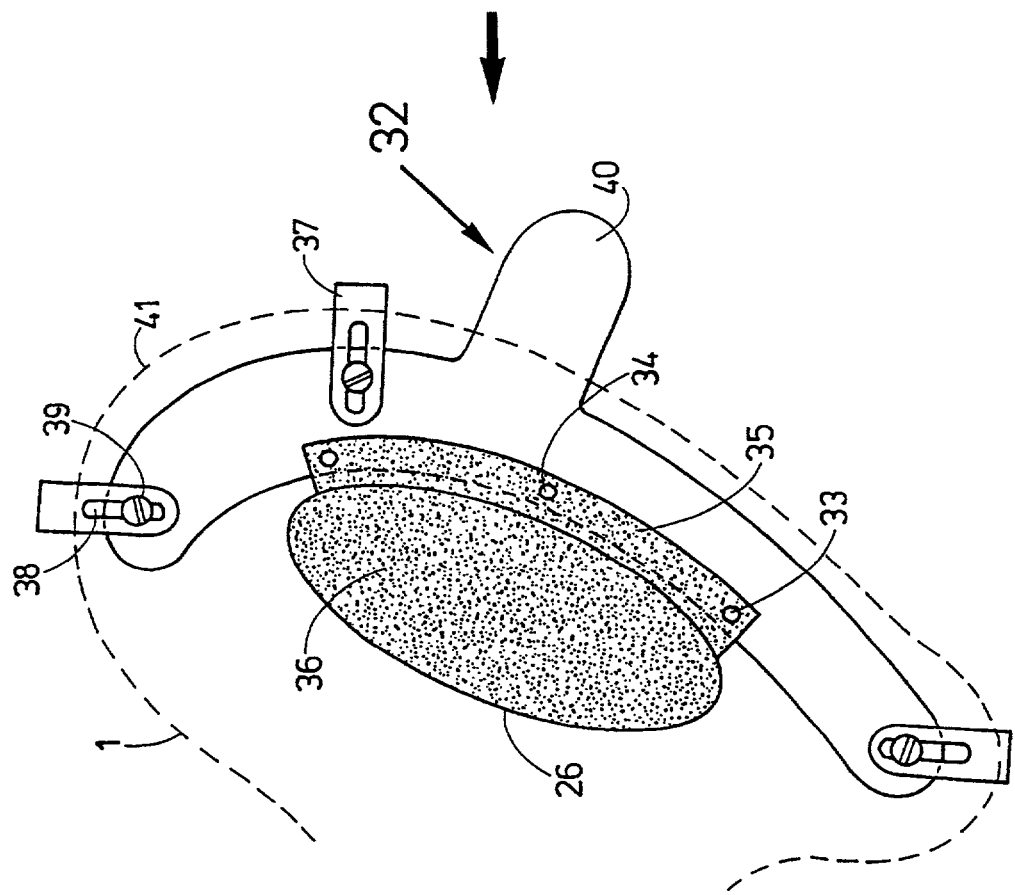

DEVICE FOR NON-INVASIVELY CORRECTING THE SHAPE OF A HUMAN EXTERNAL EAR

CROSS-REFERENCE TO RELATED APPLICATION

This application is a continuation of the national stage of PCT Application No. PCT/DK00/00421, filed Jul. 25, 2000, the content of which is expressly incorporated herein by reference thereto.

FIELD OF INVENTION

The invention relates to a device for non-invasively correcting the shape of a human external ear so that a deformed ear, such as jug-ears, will assume a desired normal shape.

BACKGROUND OF THE INVENTION

About 10% of all children have protruding ears or jug-ears which can result in teasing and psychosocial problems among children and in some cases cause reduced self-confidence. Among adults, they can result in cosmetic and/or psychological problems.

Protruding ears can also be a physical problem. Some people experience that their ears are easily exposed to sunburns in the summer. Others have difficulty in using a bike/motorcycle helmet.

In Denmark, about 2000 patients with jug-ears are operated on every year. Most often parents of children in preschool age wish to have the child operated on in order to avoid teasing when the child is sent to school.

Aures alatae often occurs within families and has a tendency to manifest itself dominantly hereditary. There is a higher incidence of jug-ears in cases of fetal alcohol syndrome, fetal hydantoin syndrome, some chromosome anomalies, such as Down's syndrome (55% have jug-ears) and Turner's syndrome, and also in case of myopathies, such as muscular dystrophy, and in case of certain cerebral affections, such as anencephaly.

Prominent ears are classified in two types, of which one is lacking or imperfectly developed/pronounced anthelix and the other is high/deep cavum concha. These two types can also occur in combination to different degrees.

The ear begin to assume the final shape in the beginning of the third fetal month where especially the development of helix takes place. This helix grows so fast that it grows past anthelix which does not really begin to be formed until the sixth fetal month. If anthelix during the rest of the fetal life cannot keep up with the growth of helix, a real, congenital deformity in form of a protrusion of the ear is formed. This is due to the fact that a certain angular bending of the auricle, corresponding to anthelix, is not present at birth. In pronounced cases, a very deep cavum concha is seen.

After that the ear grows constantly until about the age of 10 where it reaches a size that approximately corresponds to the adult ear. Eighty-fiver percent of the ear is fully grown after the age of 3. It has turned out, however, that the ear is growing on the vertical plane the entire lifetime, whereas the breadth and angle of the ear in relation to the head do not change very much after the age of 10. The best time for operation would therefore be after the age of 10.

Several experts point out, however, that it would not interfere with the growth of the ear to operate children in the preschool age. The psychosocial problems that often affect the child considerably often carry the greatest weight, and the parents therefore choose, as mentioned above, to have the children operated on before they are sent to school in order to avoid teasing.

The operational treatment of jug-ears began in the nineteenth century. Since then, many different operating methods have been developed for this purpose. Some of the operating methods are simple, others more complicated.

The disadvantage of an operation is that it often gives the patient pain—in some cases even for months or years after the operation. About 20% of the patients feel pain/soreness in the operated ear more than a year after the operation. Eight percent require further operations.

After the operation, the patients have to wear a head bandage, which looks like a turban, for 10 days so that the cartilage can heal in the desired position. Some patients have to sleep with a "nightcap" for 3 weeks before the result is satisfying.

A problem that frequently arises in connection with an operation is the formation of an abnormal cartilage fold (anthelix) with small cartilage prominences left on the ear. Such a formation can be painful to the patient and will be cosmetically unsatisfactorily.

It has been discovered that it is possible to non-surgically or non-invasively correct deformities on the auricle permanently, including jug-ears.

As far as children are concerned, the high content of estrogen in the blood explains why the ear cartilage is soft and ductile. The neonatal ear is soft and yielding. After a few days, the ear becomes more elastic and stiff which is believed to be related to the fall in the relatively high concentration of estradiol in the neonatal child.

The highest concentration of circulating estradiol in the newborn is during the first 72 hours after birth. The concentration then drops quickly. At the age of 6 weeks, the concentration of estradiol is on the same level as in older children. Tests with estrogen-injections thus result in increased yieldingness and reduced elasticity of the ear cartilage in rabbits within 24 hours of injection.

It is known that the elasticity of cartilage depends on the concentration of proteoglycan. Hyaluronic acid, a component part of proteoglycan, is increased in the concentration of estrogen and can therefore be accountable for the yieldingness of the cartilage in the neonatal ear. It is therefore within this period that congenite ear deformities, including jug-ears, can be treated the best without using surgical treatment.

Alterations of cartilage subjected to bending and external stresses have shown that ruptures of the perichondrium of the cartilage emerge, and that there subsequently will be an appositional cartilage growth which corresponds to the perichondrium on the convex side of the bending. The cartilage grows in thickness, and a permanent folding of the cartilage is obtained. This result is also best in the neonatal period.

International Publication No. WO 00/09050 discloses a fixture for non-invasively correcting jug-ears. As shown therein, the fixture is in the form of a clip for squeezing around a chosen zone of the ear in order to affect this zone for a relatively long time with compressive forces. The cartilage in the zone is thereby given a permanent deformation, as ruptures are made in the perichondrium of the cartilage with a subsequent appositional cartilage growth which causes the cartilage to be folded permanently.

This known clip is an especially suited means for non-invasively correcting a patient's external ear. The presence of the clip can, however, to some extent give the patient trouble, especially during the night when the patient is asleep. Furthermore, the clip is, despite its small size, visible, and its presence can therefore be cosmetically embarrassing to the patient.

A small child will see the clip as something unpleasant and irritating from which the child will immediately try to free itself at the risk of damaging the ear.

SUMMARY OF THE INVENTION

The invention relates to a non-invasive device for correcting a deformation in a human external ear that includes a fixture and an adhesive capable of sticking the fixture together with two fold parts on an ear that are folded about a folding line along a zone having a permanent deformation so as to correct the deformation. The fixture forms a fold with two fold parts that are stuck together with the adhesive. The fixture is formed of permanently deformable material that acts to stiffen the two fold parts while adhered thereto. The fixture may include two separate parts which are stuck together with a second adhesive.

The fixture may also include a fixing sheet having two sides and a folding edge for defining the folding line of this ear upon folding of the ear, with both sides of the fixing sheet including an adhesive for sticking the sheet together with the two fold parts of the folded ear. The fixture may include double-coated tape or a textile with adhesive on both sides, such as gauze. The fixture includes at least one detachable film for covering the adhesive prior to its application to the ear.

The invention also relates to a method of treating a permanent ear deformation that includes non-invasively applying to the external ear a fixture having an adhesive capable of sticking the fixture together with two fold parts on the ear. The fold parts are folded about a folding line along a zone having a permanent deformation so as to correct the deformation.

BRIEF DESCRIPTION OF THE DRAWINGS

The invention will be explained in greater detail below, describing only exemplary embodiments with reference to the drawing, wherein:

FIG. 16 shows the fifth embodiment in FIG. 13 of a fixture attached on a gauge for orientating the fixture in relation to the ear; and FIG. 17 shows the gauge in FIG. 16 put in position in relation to the ear with the fixture in fixing position.

DETAILED DESCRIPTION OF THE INVENTION

Figure 1:
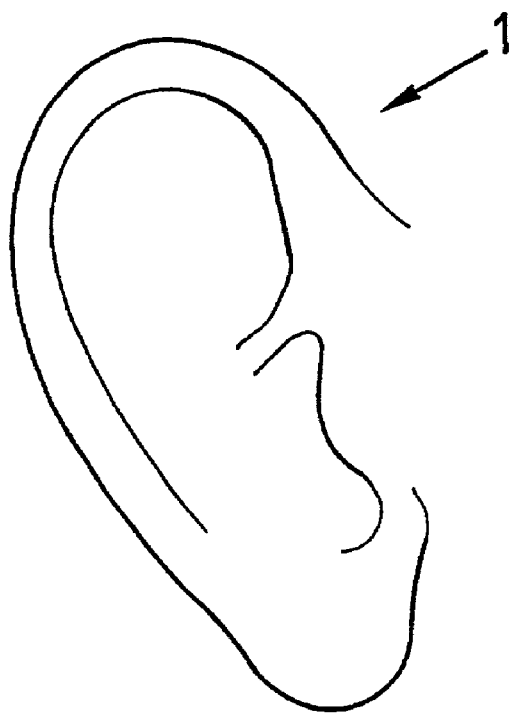
FIG. 1 is a front view of a jug-ear.

The present invention relates to a device that comprises a flat fixture with an adhesive for sticking the fixture together with two fold parts on an ear which is folded about a folding line along a zone which is to be corrected with a permanent deformation.

This fixture can advantageously be used for non-invasively correcting, for example, a small child's jug-ears which, as mentioned above, can easily be given a permanent shape within the first few weeks after birth where the concentration of estradiol is highest.

The child cannot feel the fixture which is typically fixed behind the ear so that it cannot be seen either. In addition, the fixture is so simple and easy to fix on and take off the ear that the child's mother can perform this task without difficulty at all hours that conveniently fit the child's rhythm.

In one embodiment, the fixture can have adhesive on both sides to such an extent that it can be stuck fast to both fold parts on the unfolded ear, after which the ear with the stuck fixture can be folded so that the two fold parts of the fixture are stuck together. The ear is thereby fixed in folded state as long as the fixture is stuck fast on the ear in this way.

This fixture can have a stiffener for strengthening the connection between the two fold parts of the ear in the fixing position of the fixture. The stiffener can be made of a material, such as metal, that can be permanently deformed. In this case, the stiffener can be arranged to be able to keep the fixture in fixing position so that adhesive is only necessary on the side of the fixture that faces the ear.

In a second embodiment, the fixture can include two separate parts that are stuck fast on each fold part of the unfolded ear, after which the ear with the fixture parts stuck to it can be folded so that the two parts of the fixture are stuck together and the folded position of the ear thereby is fixed.

In an especially advantageous embodiment, the fixture can be in the form of a sheet with a folding edge and a layer of adhesive on both sides. This sheet is first stuck fast on the back of the unfolded ear in the correct position, after which the outer part of the ear is folded in a positively operated way about the folding edge of the sheet and stuck fast on the sheet.

Moreover, the surface of the fixture does not have to be completely covered with adhesive. When the surface is only partially covered, the skin can breathe via the areas that are kept clear of adhesive.

In an especially simple embodiment, the fixture can merely be comprised of a double coated tape. When the fixture is comprised of a textile, such as gauze, with a layer of adhesive on both sides, the skin can advantageously breathe through the fixture.

The adhesive on the fixture can preliminarily be covered by a detachable film for protecting the adhesive and prevent unintentional sticking of the fixture. The protective film is pulled off when the fixture is to be used.

Besides protecting the adhesive, such a film can also serve as an advantageous means for positioning the fixture correctly on the unfolded ear. The film can in this case be transparent and be extending beyond the limitation of the fixture with printed coordinates for telling the operator whether or not the fixture is in the correct position in relation to the ear. The coordinates that are best suited for an ear with a given configuration can be given in the accompanying instructions.

The fixture can also be positioned in relation to the unfolded ear by means of a gauge having means for detachably keeping the fixture and a stop for supporting the gauge against the helix of the ear so that a new fixture is always positioned on the same spot on the ear as the previous fixtures. This ensures that the folding line of the ear always will be along the zone that is to be corrected with a permanent deformation.

The stop of the gauge can furthermore be arranged in such a way that they can be set to fit the configuration of a given ear.

Referring now to the drawings, FIG. 1 is a front view of a jug-ear 1. The characteristic feature of the ear is that it lacks the anthelix that is found on a normal ear. The deformity is in different ways very inconvenient for a person having such a jug-ear, and it is therefore desirable to form an anthelix on the jug-ear so that it will assume a normal shape.

Figure 2:
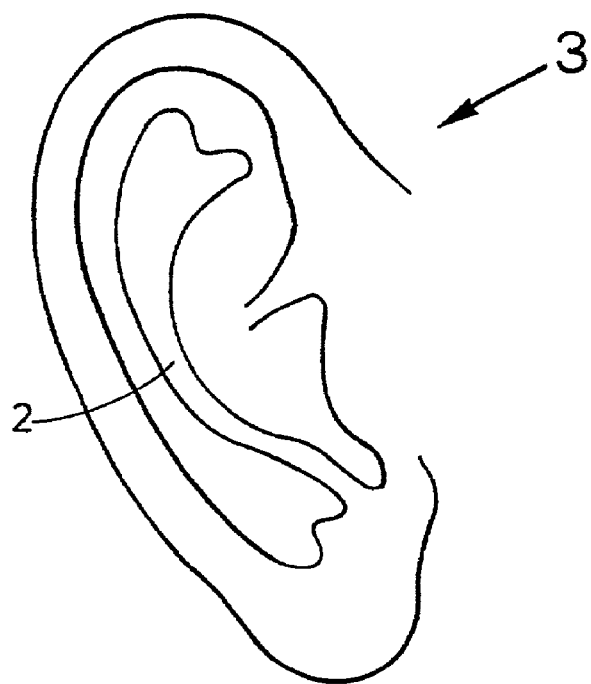
FIG. 2 shows the ear in FIG. 1 after having been treated with the fixture according to the invention.

In FIG. 2, the ear has been non-invasively treated with a fixture according to the invention whereby an anthelix 2 has been formed that has given the ear 3 the desired normal shape.

Figure 3:
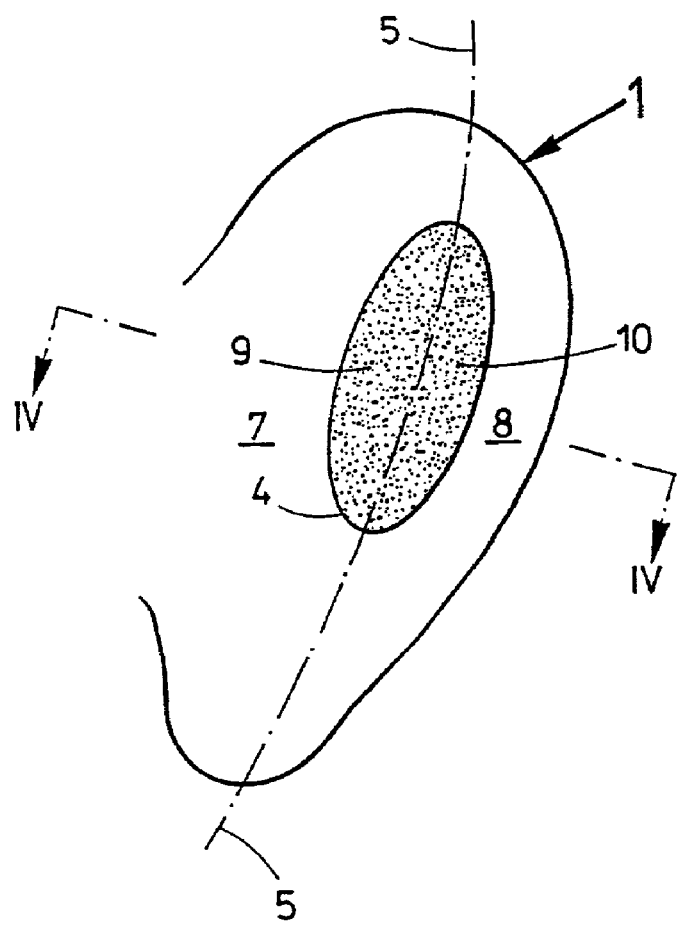
FIG. 3 is a rear view of the jug-ear in FIG. 1 with a fixture stuck fast to it according to the invention.
Figure 4:
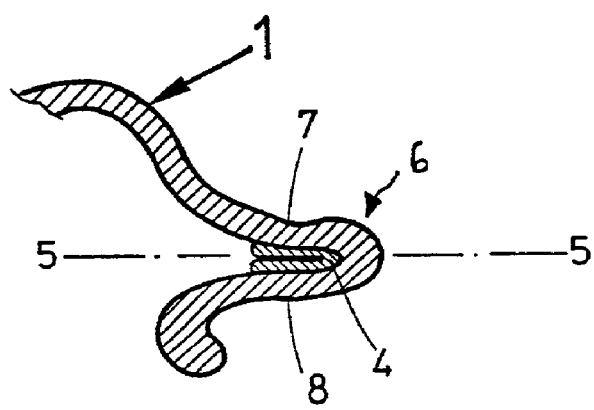
FIG. 4 is a sectional view taken along the line IV—IV in FIG. 3 but with the ear in folded state and the fixture in fixing position.

FIGS. 3–4 are diagrammatic views of how this anthelix 2 is formed. In FIG. 3, now showing the jug-ear from the rear, a flat, flexible fixture 4 is stuck fast behind the ear 1 by means of an adhesive (not shown) applied on the side of the fixture facing the ear. The outer side of the fixture is also applied with an adhesive (not shown).

In FIG. 4, the ear is folded along a folding line 5—5 forming a fold 6 with an inner fold part 7 and an outer fold part 8. At the same time, the flat, flexible fixture 4, which is stuck fast on the ear, has also been folded so that an inner part 9 and outer part 10 of the outer side of the fixture are facing each other. When the two fold parts 7,8 of the ear are finally squeezed together about the fixture, the two parts 9,10 of this fixture are stuck together by means of the adhesive on the outer side of the fixture. The ear is thereby fixed in the folded position shown.

When the ear is kept fixed in this way for some time, the zone along the folding line 5—5 gradually undergoes a process that gives it a permanent deformation whereby the zone finally will remain standing in a fold forming the desired anthelix.

The fixture can with great advantage be used for non-invasively correcting a small child's jug-ears which easily are permanently deformed within the first few weeks after birth where the concentration of estradiol is highest. The child hardly notices the presence of the fixture and has moreover difficulty in getting hold of it as it is hidden between the two fold parts of the ear fold. The fixture is easy to fix on the ear and to remove again. When the child is to be washed behind the ear, the fixture is removed and afterwards replaced with a new one for continuation of the treatment.

Figure 5:
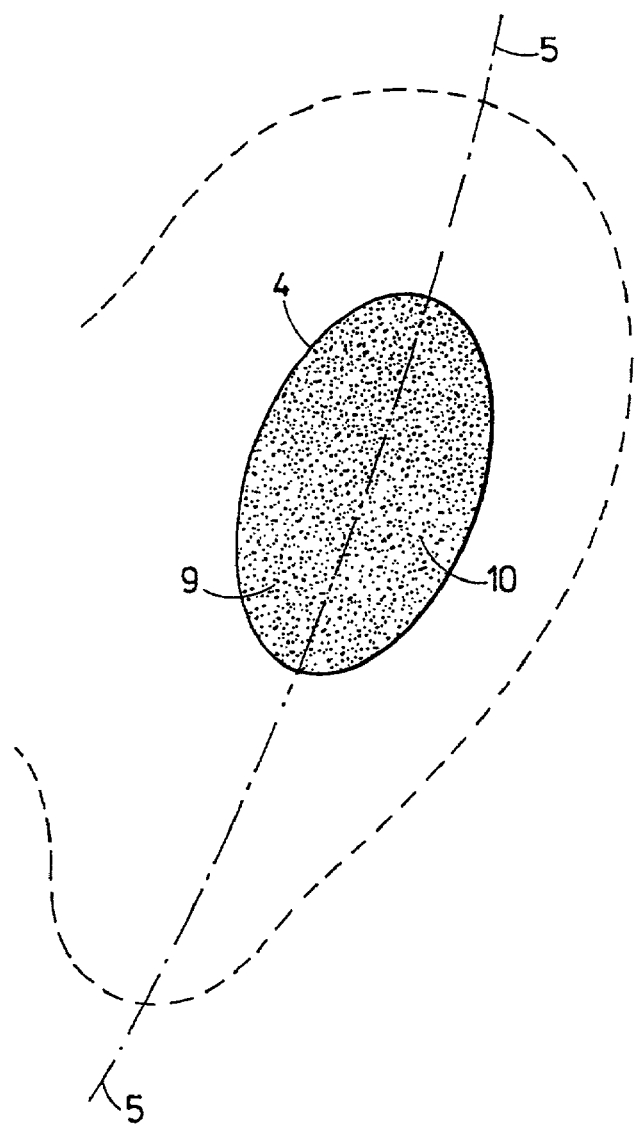
FIG. 5 is a rear view of a first embodiment of a fixture according to the invention stuck on a jug-ear.
Figure 6:
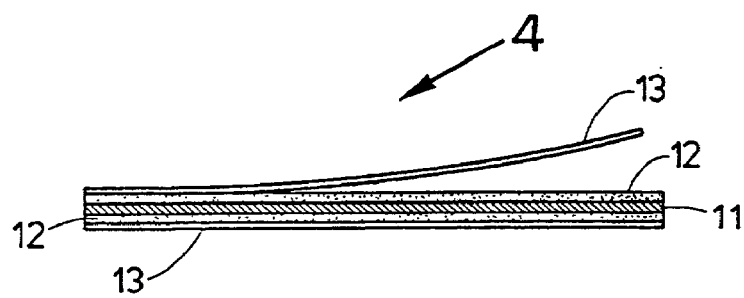
FIG. 6 is on a larger scale a sectional view through the fixture in FIG. 5.

FIG. 5 shows the same fixture 4 as in FIG. 3 stuck on the back of a jug-ear 1 which is to be corrected, and FIG. 6 is on a larger scale a sectional view through this fixture. As it can be seen, the fixture 4 is in this case comprised of a flexible foil 11 with a layer of adhesive 12 applied on both sides of the foil. The adhesive is furthermore protected by a film 13. When the fixture is to be used, the film 13 is first pulled off one side of the fixture. Then the fixture is stuck on the back of the jug-ear 1 by means of the adhesive 12 on this side, as shown in FIGS. 3 and 5. Then the ear is folded and fixed in the folded position as described above with reference to FIG. 4.

Figure 7:
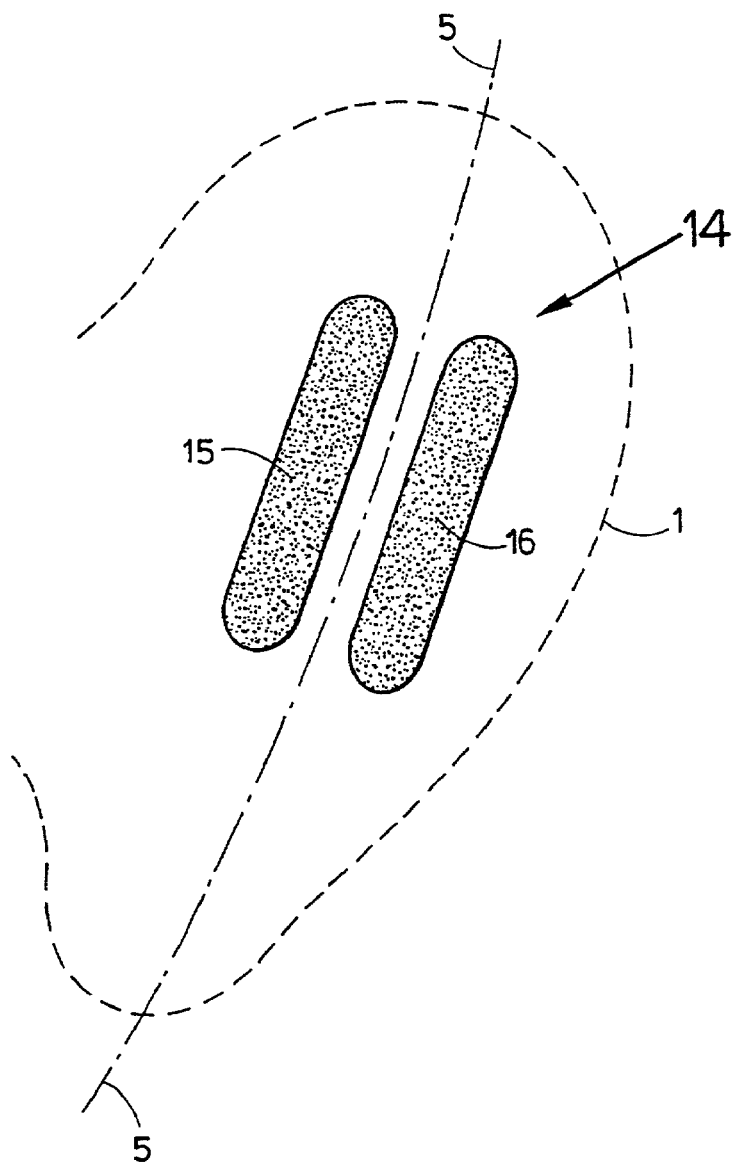
FIG. 7 is a rear view of a second embodiment of a fixture according to the invention stuck on a jug-ear.
Figure 8:
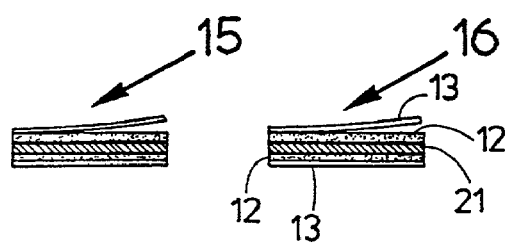
FIG. 8 is on a larger scale a sectional view through the fixture in FIG. 7.

FIGS. 7–8 show a variant of the embodiment in FIGS. 3–6. In this case, the fixture 14 is, however, comprised of two separate parts 15 and 16 which are stuck together when the ear is folded. This fixture functions in the same way as the embodiment described above with reference to FIGS. 3–6, and it is constructed in the same way with a flexible foil 11 and a layer of adhesive 12 applied on both sides of the foil and protected by a film 13.

Figure 9:
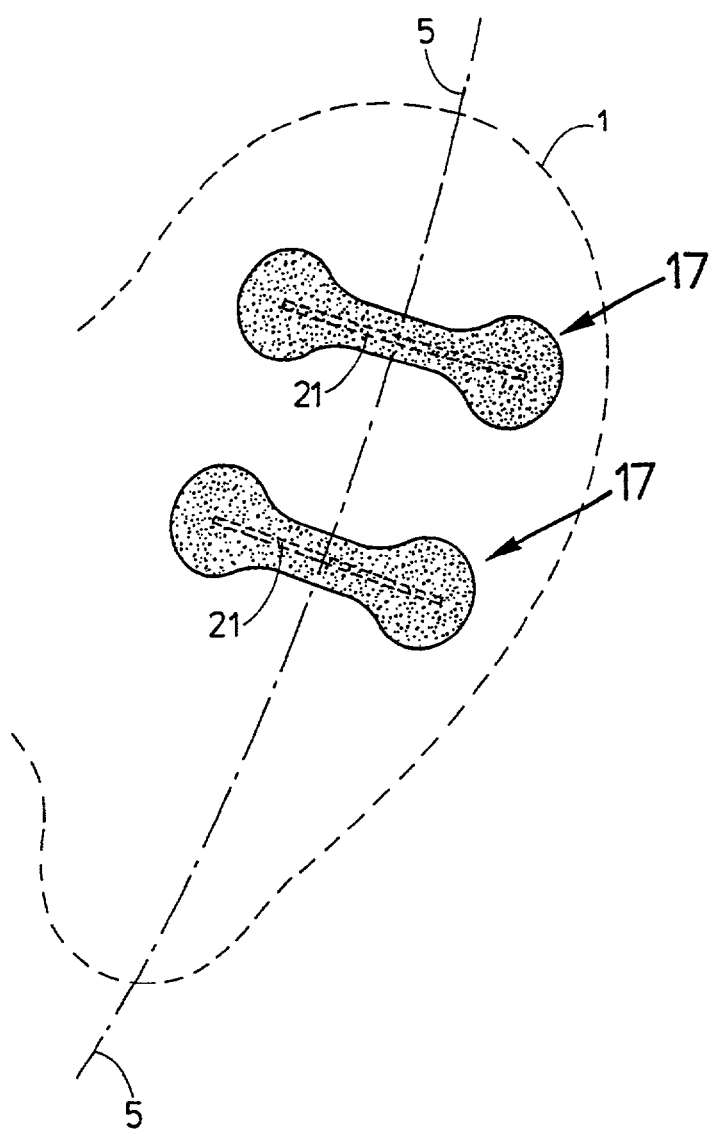
FIG. 9 is a rear view of a third embodiment of a fixture according to the invention stuck on a jug-ear.
Figure 10:
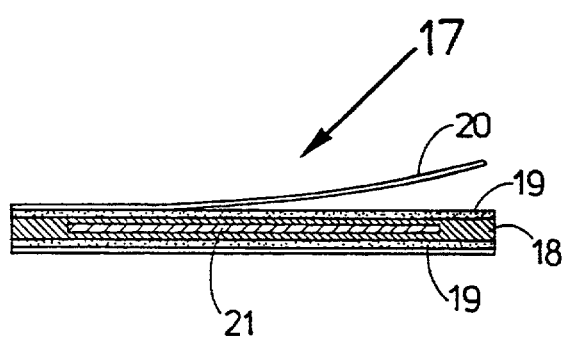
FIG. 10 is on a larger scale a sectional view through the fixture in FIG. 9.

FIGS. 9–10 show an embodiment of a fixture 17 in two smaller parts, each constructed in the same way as shown in FIGS. 3–6 with a flexible foil 18 and a layer of adhesive 19 applied on both sides of the foil and protected by a film 20. In this case, the fixture is provided with a metal stiffener 21 for strengthening the connection between the two fold parts of the ear in the fixing position of the fixture. The stiffener is bent at the same time as the ear is folded whereby it will contribute to or completely take over the task of fixing the ear in its folded position. In the latter case, adhesive on the side of the fixture that faces the ear will only be needed just as this embodiment of the fixture according to the invention also can be used by being stuck on the front of the ear (not shown).

Figure 11:
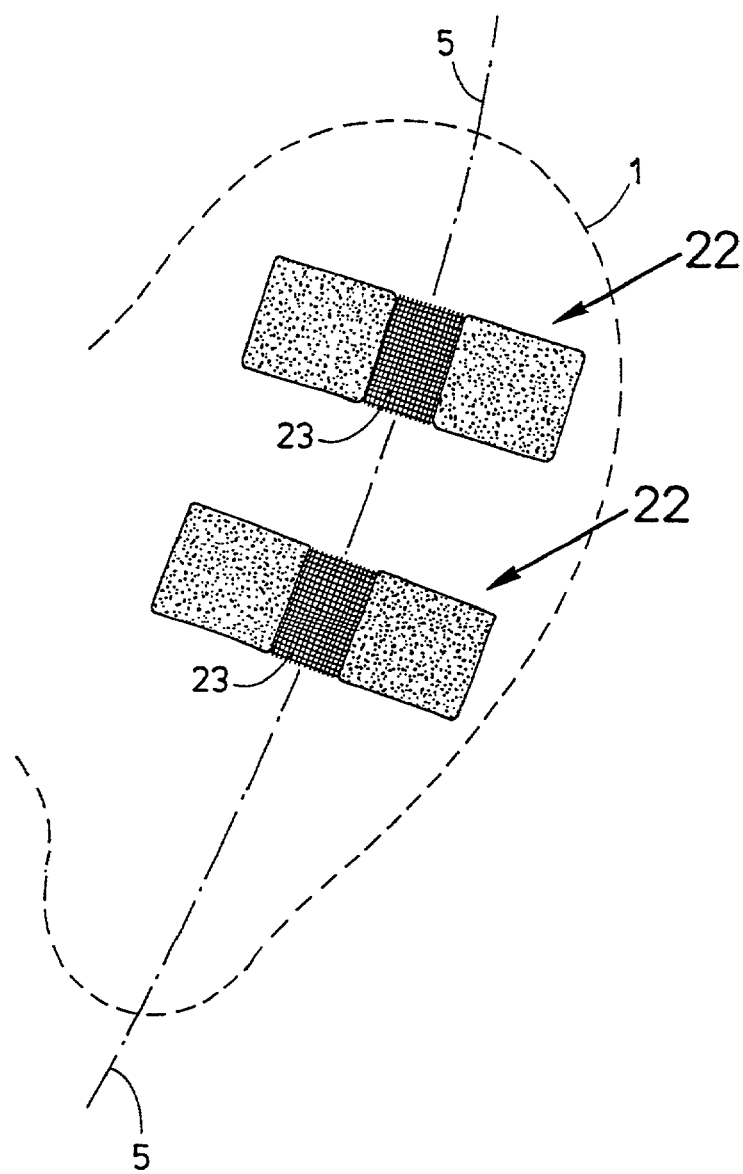
FIG. 11 is a rear view of a fourth embodiment of a fixture according to the invention stuck on a jug-ear.
Figure 12:
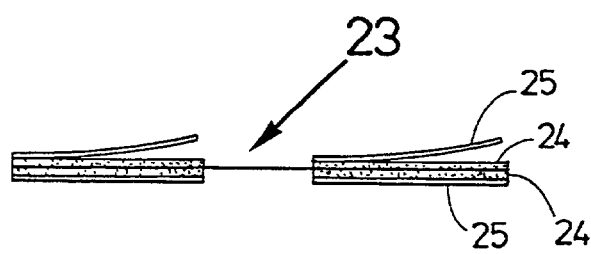
FIG. 12 is on a larger scale a sectional view through the fixture in FIG. 11.

FIGS. 11–12 show a second embodiment of a fixture 22 divided into two smaller parts. The flexible foil has, however, now been replaced by a piece of gauze 23 with an adhesive 24 on both sides and a film 25 for protecting the adhesive on both sides. The gauze 23 allows the skin to breathe through the fixture. This advantage is advanced by the fact that the sides of the gauze in this case are only partly covered with adhesive.

Figure 13:
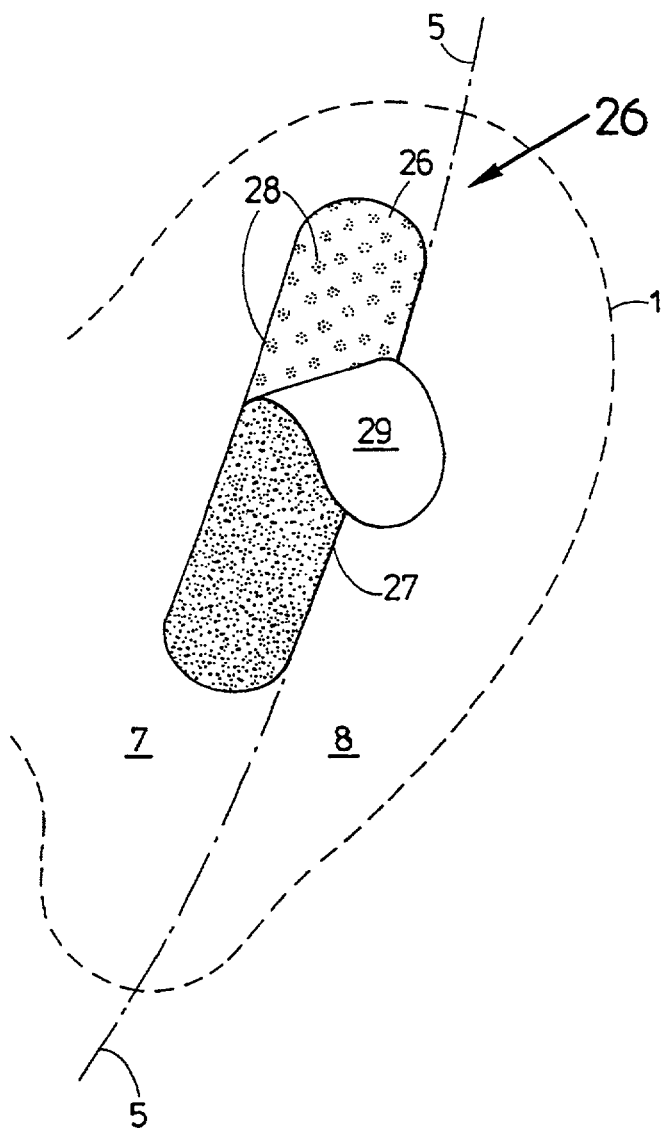
FIG. 13 is a rear view of a fifth embodiment of a fixture according to the invention stuck on a jug-ear.
Figure 14:
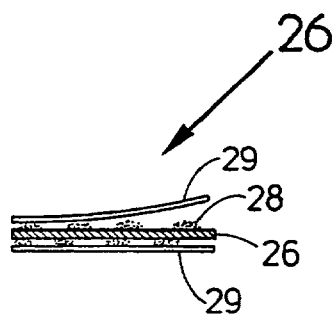
FIG. 14 is on a larger scale a sectional view through the fixture in FIG. 13.

FIGS. 13–14 show an especially advantageous embodiment of a fixture 26 according to the invention. In this case, the fixture is comprised of a relatively thin fixing sheet 26 having a shape that matches or is somewhat smaller than the inner fold part 7 (FIG. 4) of the fold 6, and a folding edge 27 which in the fixing position shown follows the desired folding line 5—5 of the fold. The thin fixing sheet 26 is on both sides partially applied with an adhesive 28, each covered with a protecting film 29.

When this fixture is to be used, the protective film 29 is first pulled off one side of the fixing sheet, after which the sheet by means of the adhesive on this side is stuck fast on the back of the jug-ear with the folding edge 27 placed along the folding line 5—5. Then the film 29 is pulled off the outer side of the stuck fixing sheet as indicated in FIG. 13, after which the outer fold part 8 of the ear is folded about the folding edge 27 of the sheet and stuck fast on the sheet. The presence of the folding edge 27 of the fixing sheet 26 ensures that the jug-ear 1 easily and effortlessly can be folded in the exact same way every time, as the folding line during this quite simply is forced to follow the contour of the folding edge. The shown partial application of the adhesive 28 on the fixing sheet 26 ensure that the skin can breathe via the areas that are kept clear of adhesive.

Figure 15:
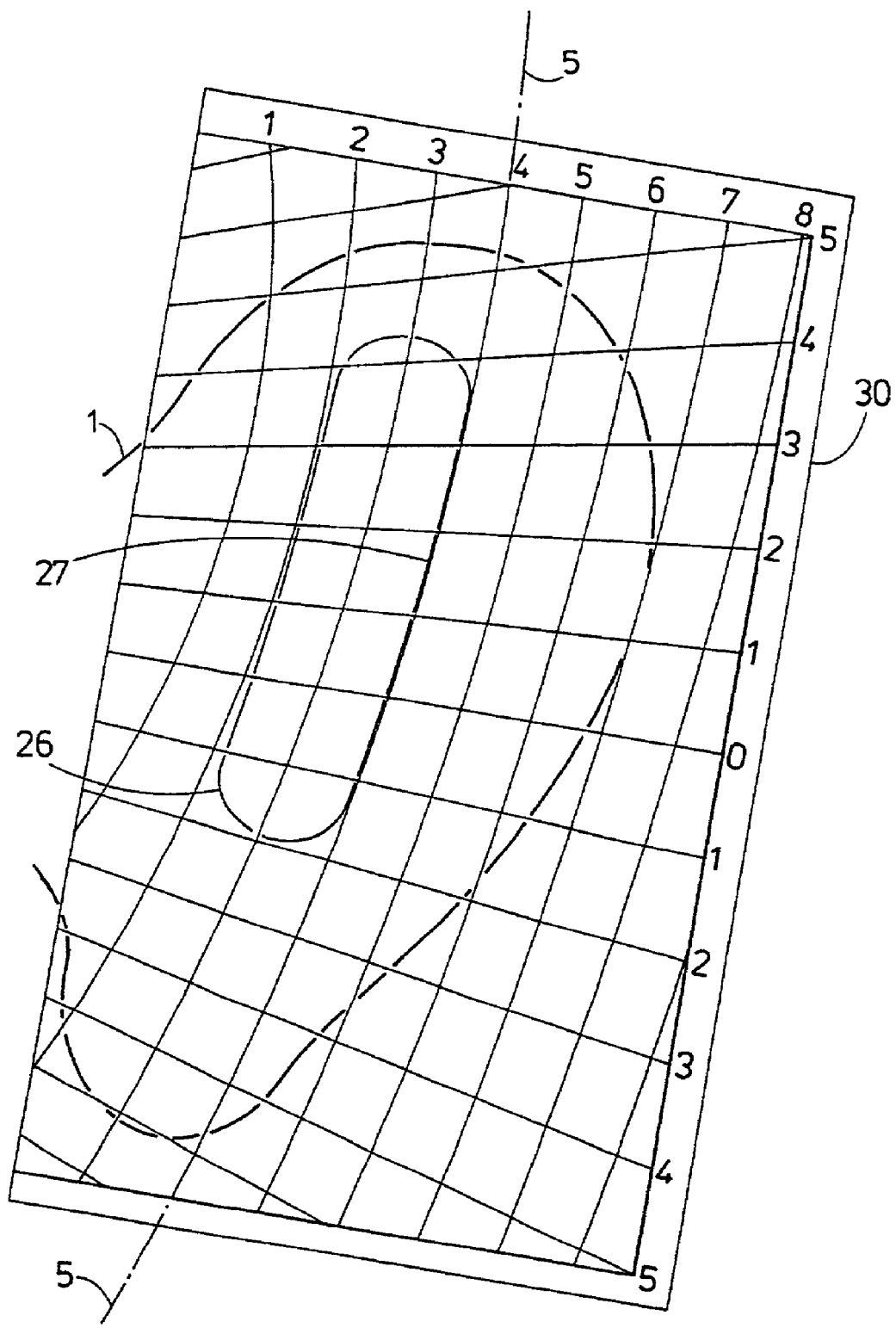
FIG. 15 shows the fifth embodiment in FIG. 13 of a fixture with a projecting transparent film provided with coordinates for orientating the fixture in relation to the ear.

In FIG. 15, the fixing sheet 26 is again shown in stuck state on the back of the jug-ear 1. But in this case, the outer protective film 30 is extending beyond the limitation of both the sheet and the unfolded ear. The film is made of a transparent material and is imprinted with a coordinate system 31 for orientating the fixing sheet 26 in relation to the ear as the operator during this places the coordinate system in such a way that specific coordinates will be on level with specific points along the contour of the ear. The line 1—1 corresponds to the desired folding line 5—5 of the ear.

FIG. 16 shows a forked gauge 32 for being able to reliably place the sheet 26 in the same correct position on the jug-ear 1 every time. On the side facing the fixing sheet 26, the gauge 32 has three transverse pins 33 for engaging with corresponding holes 34 in a projecting tab 35 on the outermost protective film 36. In FIG. 16, the sheet 26 is detachably fastened in this way on the gauge 32. On the opposite side of the gauge than the side facing the sheet, the gauge is provided with three stops 37 with slots 38 and screws 39 for setting the stop in the desired position in relation to the gauge 32. The gauge has a handle 40 that the operator (not shown) conveniently can hold on to when the gauge is to be used.

In FIG. 17, the operator has placed the gauge with the fixed sheet 26 on the back of the unfolded jug-ear 1 so that the stop just touches the helix 41 of the ear. The innermost protective film has in advance been pulled off the fixing sheet 26 which now is in the correct position on the ear and therefore can with a light pressure be immediately stuck fast on the ear by means of the adhesive 28 in the fixing sheet 26.

Then the gauge is removed whereby the outermost protective film 36 which with the projecting tab 35 is still stuck on the gauge is pulled off the fixing plate so that the outermost adhesive layer 28 on this is uncovered, after which the ear is folded about the folding edge 27 of the sheet and fixed in folded position as described above with reference to FIGS. 13–14. Finally, the film 36 is removed from the gauge 32. The operation is finished.

The gauge effectively ensures that a new fixing plate 26 is always stuck fast on the exact same spot on the ear as the previous fixing sheets so that a well-shaped anthelix is formed exactly on the desired spot on the ear. If the fixing sheet is placed on a different spot on the ear than the previous, an incipient deformation will appear on the new spot and perhaps on a different new spot at the next replacement of the fixing sheet again, and so on.

Such a more or less random placing of the fixing sheet on the ear will cause the operation to take an unduly long time to form an anthelix and that the eventually formed anthelix will be deformed and ugly.

The coordinate system in FIG. 15 and the gauge in FIGS. 16–17 therefore constitute important elements of the device according to the invention for correcting a human external ear.

The design of both the gauge and the coordinate system only are to be taken as examples, and that both can be designed in any other expedient way within the scope of the invention. For instance, the stop of the gauge can be arranged to during the fixing operation support against the head and the root of the ear, corresponding to the peak of the cephaloauricular angle, in stead of against the helix of the ear.

The coordinate system can merely be marked with numbered points. These points can possibly be formed as holes for placing of pegs (not shown) whereby the projecting outermost protective film 30 on the fixing sheet 26 also can be used as gauge with the pegs as stop. The mentioned embodiments of fixtures are also to be taken as examples. In some cases, they can furthermore be arranged to act on the front of the ear or to act between the ear and the head.

The invention is described above and shown in the drawing on the exemplary assumption that it was used for forming an anthelix on a jug-ear. The fixture can, with just as great an advantage, be used for correcting other deformities on a human external ear, and the fixture can obviously be used on both children and adults.

At surgical operation for correcting a deformed ear, including jug-ears, an incision is made behind the ear which subsequently is sutured. Then the ear is kept in the desired position in relation to the head for 10 days by means of a head bandage so that it can heal in this position.

This head bandage can often be physically and cosmetically embarrassing to the patient. In stead, the operated ear can conveniently and without any inconveniences of any kind be fixed in the position by means of the fixture according to the invention. In this case, the fixture could at the same time act as a plaster covering the incision. The plaster can then be arranged in such a way that the suture can be spared.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method of treating a permanent ear deformation which comprises non-invasively applying to the external ear of a human patient in need of such treatment a flat fixture that includes an inner part and an outer part, with the inner side of the inner part stuck on an inner fold part of the back of the ear, the inner side of the outer part arranged to be stuck on an outer fold part on the back of the ear, and the outer side of the inner and outer parts arranged to be stuck together when facing each other to form a fold about a folding line along a zone having a permanent deformation so that said inner and outer part are kept fixed in folded position to correct the deformation.

2. The method of claim 1, wherein the fixture comprises a permanently deformable material that acts to stiffen the two fold parts while adhered thereto.

3. The method of claim 2, wherein the material that can be permanently deformed comprises at least one metal.

4. The method of claim 1, wherein the fixture is comprised of two separate parts.

5. The method of claim 4, wherein the two separate parts in the fixing position are stuck together with an adhesive.

6. The method of claim 1, wherein the fixture is in form of a fixing sheet with a folding edge for upon folding of the ear defining the folding line of this ear, and both sides of the fixing sheet are applied with an adhesive for sticking the sheet together with the two fold parts of the folded ear.

7. The method of claim 1, wherein the fixture consists of a textile with adhesive on both sides.

8. The method of claim 7, wherein the textile is gauze.

9. The method of claim 1, wherein the fixture is covered with at least one detachable film for preliminarily covering the adhesive.

10. The method of claim 9, wherein the film extends beyond the fixture and is provided with coordinates for positioning the fixture in relation to the unfolded ear.

11. The method of claim 1, wherein the film comprises a gauge for positioning the fixture in relation to the unfolded ear.

12. The method of claim 1, wherein the fixture comprises a double-coated tape.

13. The method of claim 1, further comprising folding the ear along the folding line before applying the fixture thereto.

14. The method of claim 1, wherein the fixture is applied so that a folding edge of the fixture folds along the folding line.

15. The method of claim 1, further comprising sticking the inner side of the outer part on the outer fold part on the back of the ear.

16. The method of claim 15, further comprising, with the inner and outer parts stuck to the ear, sticking the inner and outer parts of the applied fixture together by folding the ear to form the fold about the folding line along the zone having the permanent deformation so that said inner and outer part are kept fixed in folded position to correct the deformation.

17. The method of claim 1, further comprising positioning the fixture on the ear using coordinates on a detachable film provided on the fixture.

18. The method of claim 1, wherein the fixture comprises a first adhesive capable of sticking the inner and outer parts together, and comprises a gauge for positioning the fixture in relation to the unfolded ear.

* * * * *

UNITED STATES PATENT AND TRADEMARK OFFICE
CERTIFICATE OF CORRECTION

PATENT NO. : 7,093,600 B2 Page 1 of 1
APPLICATION NO. : 10/050618
DATED : August 22, 2006
INVENTOR(S) : Sorribes It is certified that error appears in the above-identified patent and that said Letters Patent is hereby corrected as shown below:

<u>Title Page</u>:
Item (30) Foreign Application Priority Data, change "Jul. 27, 1909" to
-- Jul. 27, 1999 --.

Signed and Sealed this

Thirty-first Day of October, 2006

JON W. DUDAS
*Director of the United States Patent and Trademark Office*